United States Patent
Arick et al.

Patent Number: 5,885,242
Date of Patent: Mar. 23, 1999

[54] APPARATUS FOR EQUALIZING THE PRESSURE IN THE MIDDLE EAR

[76] Inventors: Daniel Arick, 20 W. 64th St., Apt. 17D, New York, N.Y. 10023; Shlomo Silman, 3030 Emmons Ave., Apt. 3R, Brooklyn, N.Y. 11235

[21] Appl. No.: 787,888

[22] Filed: Jan. 23, 1997

Related U.S. Application Data

[63] Continuation of Ser. No. 419,379, Apr. 10, 1995, abandoned, which is a continuation-in-part of Ser. No. 166,314, Dec. 10, 1993, Pat. No. 5,419,762, which is a continuation-in-part of Ser. No. 109,173, Aug. 19, 1993, abandoned.

[51] Int. Cl.$^6$ .......... A61M 37/00; A61M 11/00; A61M 15/08
[52] U.S. Cl. .......... 604/626; 128/207.18; 604/94
[58] Field of Search .......... 604/23, 26, 54, 604/94, 275; 128/200.12, 200.22, 204.21, 205.18, 207.18

[56] References Cited

U.S. PATENT DOCUMENTS

| | | |
|---|---|---|
| 1,533,618 | 4/1925 | Taylor, Jr. . |
| 1,599,787 | 9/1926 | Perkiss .......... 604/275 |
| 2,516,762 | 7/1950 | Dwyer .......... 128/207.18 |
| 3,749,083 | 7/1973 | Mathers, Jr. .......... 604/26 |
| 4,542,740 | 9/1985 | Kleinschmidt et al. .......... 128/204.21 |
| 4,771,769 | 9/1988 | Hegemann et al. .......... 128/200.22 |
| 5,394,866 | 3/1995 | Ritson et al. .......... 128/200.14 |
| 5,687,715 | 11/1997 | Landis et al. .......... 604/94 |

Primary Examiner—Wynn Wood Coggins
Assistant Examiner—Michael J. Hayes
Attorney, Agent, or Firm—McAulay Nissen Goldberg Kiel & Hand

[57] ABSTRACT

An apparatus for equalizing pressure in a middle ear includes a hand held air source for providing a continuous flow of air at a predetermined rate and a tapered sealing nostril plug adapted to be inserted into a nostril. The tapered nostril plug has a channel therethrough for delivering the continuous flow of air. The channel of the tapered plug is adapted to be placed in communication with the air source, and a controller is coupled to the air source to limit the pressure provided at the channel of the nostril plug to substantially no more than 3.0 pounds per square inch.

7 Claims, 5 Drawing Sheets

APPARATUS FOR EQUALIZING THE PRESSURE IN THE MIDDLE EAR

RELATED APPLICATIONS

This application is a continuation of application Ser. No. 08/419,379 filed Apr. 10, 1995, now abandoned, which is a continuation-in-part of Ser. No. 08/166,314 filed Dec. 10, 1993 now U.S. Pat. No. 5,419,762, which in turn is a continuation-in-part of Ser. No. 08/109,173 filed Aug. 19, 1993 now abandoned.

BACKGROUND OF THE INVENTION

The present invention is related to an apparatus for equalizing the pressure in the middle ear. More specifically, the present invention relates to a portable, hand-held apparatus which may be used to equalize the pressure in the middle ear.

An imbalance between the pressure in the middle ear and the ambient pressure can result in the sensation of ear clogging, generally referred to as Eustachian Tube Dysfunction (ETD). Patients often suffer from ETD as a result of a cold, allergies, or descent in an aircraft from high altitude. ETD, if not treated or naturally relieved, may lead to chronic traumatic inflammation of the middle ear, also known as aerotitis media, aviator's ear, otic barotrauma, barotitis media, and aviation otitis.

The middle ear cavity communicates with the pharynx via the Eustachian tube. The Eustachian tube is usually closed, however, it opens during swallowing and yawning. in order to equalize the pressure in the middle ear the Eustachian tube must be opened.

Sufferers of ETD and aerotitis media have attempted to relieve any discomfort due to the affliction by yawning, swallowing, chewing gum, and closing the nostrils and blowing lightly to attempt to equalize the pressure in the middle ear. These methods, however, yield unpredictable results.

In extreme cases, fluid may build up behind the ear drum leading to complications including hearing loss. While some sufferers of ETD and aerotitis media have minimal discomfort which lasts merely during the descent or ascent in an airplane, others have more serious symptoms. In these cases, it is often necessary for a sufferer of aerotitis media to visit an Otolaryngologist who manually equalizes the middle ear pressure with the environment.

The Otolaryngologist normally employs one of two methods to equalize the pressure in the middle ear. The first method employed involves the use of steroids and/or antibiotics to alleviate any discomfort. An alternate method, known as the Politzer maneuver, requires the Otolaryngologist to use a tube to force air from a balloon into the sufferer's nose. When the sufferer swallows, the Eustachian tube opens, and air is forced into the middle ear to equalize the middle ear pressure. The Politzer maneuver is difficult to administer because the delivery of the air from the balloon by the doctor must occur simultaneously with swallowing by the patient.

It is an object of this invention to provide a portable, compact, hand-held apparatus which may be easily transported to alleviate any discomfort of an ETD or aerotitis media sufferer.

BRIEF DESCRIPTION

A hand held device having an air flow source is provided. The air flow source is connected to a nostril plug having a channel therethrough. The air flow source is activated to deliver a relatively constant flow of air through the channel in the nostril plug. During use, the sufferer, while holding the device in one hand, inserts the nostril plug into one of his nostrils to create a seal. Once the nostril plug is sealingly inserted into one nostril, the sufferer uses his other hand to close his other nostril. The other nostril is closed by applying pressure to the outer side of the nostril and pushing it to seal the second nostril. With one nostril sealingly engaging the nostril plug and the second nostril sealed-off, the sufferer activates the air source, preferably using one of the fingers on the hand holding the device, to supply a constant flow of air into the nostril through the channel. The sufferer must then swallow to open the Eustachian tube. During the time that the Eustachian tube is open, air delivered from the air flow source enters the middle ear through the Eustachian tube and results in ear pressure equalization. Since the flow of air is constant, the need for the sufferer to time his swallowing with the delivery of air is minimized.

DETAILED DESCRIPTION OF THE INVENTION

Figure 1:
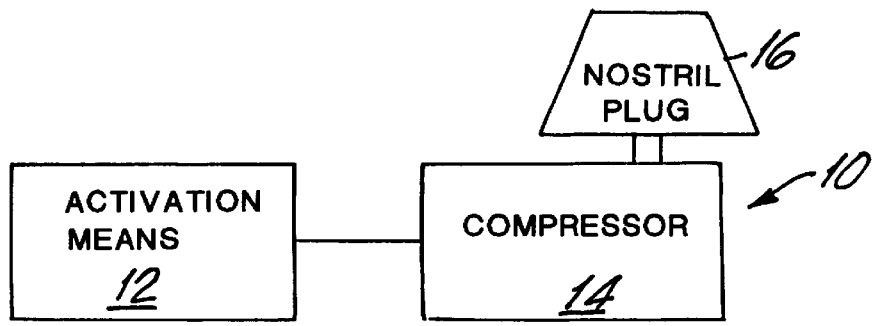
FIG. 1 is a block diagram illustrating the present invention.

Referring to FIG. 1, a presently preferred embodiment of pressure equalizing apparatus 10 according to the present invention includes activation means 12, compressor 14 and nostril plug 16.

Figure 2:
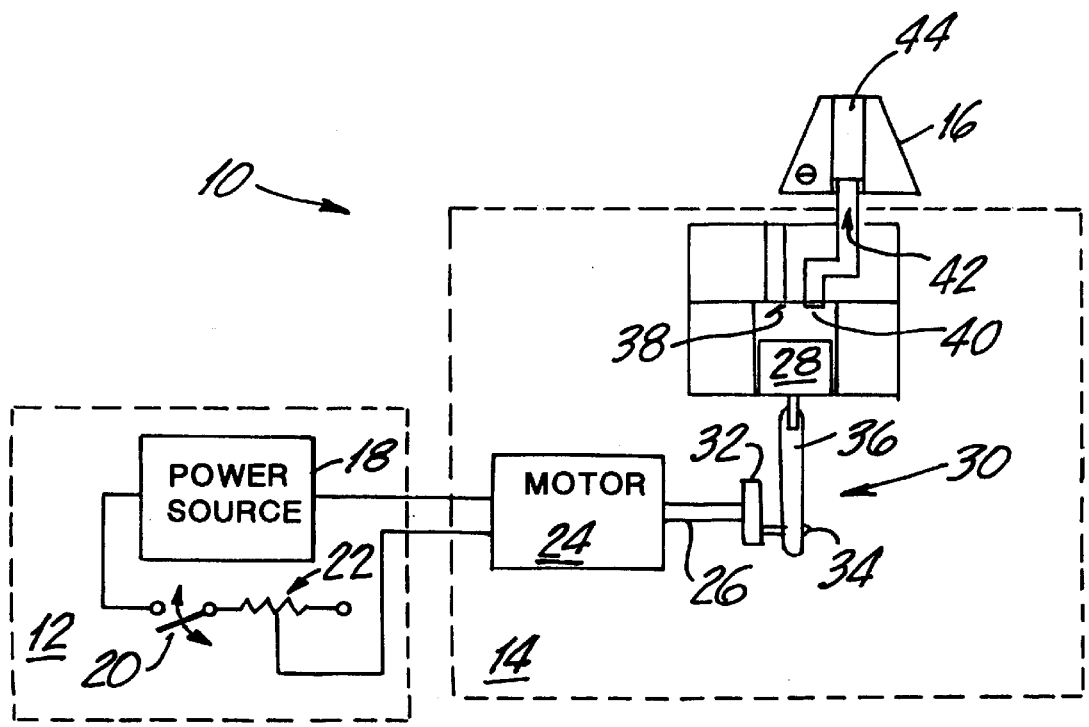
FIG. 2 is a schematic/cross-sectional view of a first embodiment of the present invention.

Referring to FIG. 2, activation means 12 includes power source 18, switch 20 and power variation device 22. Compressor 14 is activated by activation means 12. More specifically, compressor 14 includes motor 24 having motor shaft 26. Motor shaft 26 is connected to piston 28 through pivoting linkage 30. Pivoting linkage 30 includes rotating disk 32 having pin 34 extending transversely therefrom, and arm 36. Pin 34 pivotally engages arm 36. Arm 36 pivotally drives piston 28 upon rotary motion of shaft 26 and disk 32. Oscillation of piston 28 effects operation of flutter valves 38 and 40. Deflection of flutter valves 38 and 40 operate to create air flow through exit port 42. Exit port 42 communicates with channel 44 in nostril plug 16.

Figure 3:
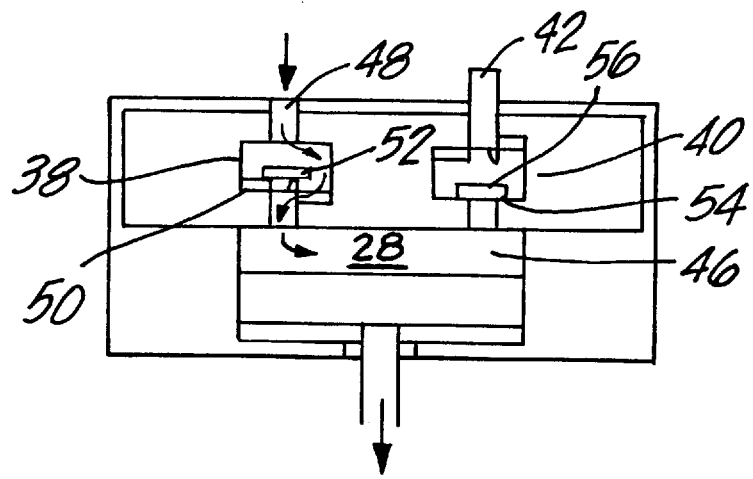
FIG. 3 is a cross-sectional view illustrating operation of the flutter valves during the downward stroke of the piston.

Referring to FIG. 3, during the downward stroke of piston 28, flutter valve 38 operates to allow air to be drawn into chamber 46 through port 48. More specifically, shoulder 50, having radially extending ridges and channels, prevents disk 52 from sealing off port 48 during the downward stroke of piston 28. Simultaneously, flutter valve 40 prevents the drawing of air through exit port 42. Shoulder 54 is relatively smooth, allowing disk 56 to provide a seal to prevent the drawing of air through exit port 42.

Figure 4:
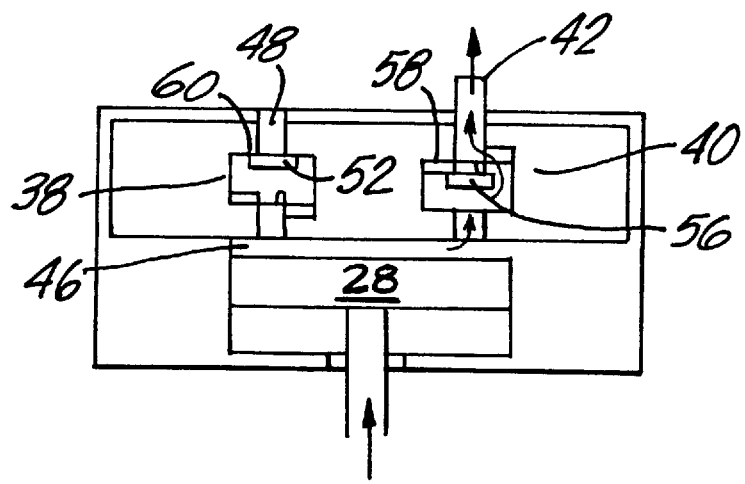
FIG. 4 is a cross-sectional view illustrating operation of the flutter valves during the upward stroke of the piston; and, FIG. 5 is a side plan view of an alternate embodiment of the present invention which includes a cross-sectional view of a nostril plug.

Referring to FIG. 4, during the upward stroke of piston 28, air which was previously drawn into chamber 46 during the downward stroke of piston 28, is expelled through exit port 42 by operation of flutter valve 40. During the upward stroke of piston 28, shoulder 58 and disk 56 operate similar to disk 52 and shoulder 50 during the downward stroke. Simultaneously, flutter valve 38 prevents the expulsion of air through port 48. During the upward stroke of piston 28, disk 52 and shoulder 60 operate similar to disk 56 and shoulder 54 during the downward stroke of piston 28.

Compressor 14 provides a rapid succession of pulses of air as a function of the rotational speed of the motor. The succession of pulses is therefore so rapid that a continuous air flow is delivered in this context. In use, the air flow is continuous for the period of the procedure which may vary from a few seconds to several minutes. The apparatus should provide the user with sufficient control over the duration of the continuous air flow period to minimize difficulties associated with the timing of the delivery of air to the patient and swallowing. The requisite duration may be either user-defined by turning the device on or off, or apparatus-defined, i.e., intermittently providing continuous air flow over a timed interval. While the air flow provided is continuous, the air flow rate need not be constant and is likely to vary as a function of the back-pressure created in the patient's nasal cavity.

Activation means 12 and compressor 14 are combined to provide a constant air flow which is bounded by a maximum constant air pressure. As used herein, the term "air pressure" is intended to mean the constant air pressure as measured by a Bourdon-spring type pressure gage.

Switch 20 may include a locking element to hold switch 20 in the on position. In an alternate embodiment, switch 20 may be spring biased and thus, require pressure to maintain the on position. Additionally, power variation device 22 acts to vary the power supplied to motor 24, thereby varying the rotational speed of shaft 36 and thus, regulating air pressure supplied through exit port 42 and nostril plug channel 44. Power source 18 may include batteries.

Pressure equalizing apparatus 10 is operated by inserting nostril plug 16 into a first nostril. The operator creates a seal by inserting nostril plug 16 into the first nostril. The operator's second nostril is collapsed using a free hand to prevent leakage therethrough. Activation means 12 is used to control compressor 14. Accordingly, air is supplied through nostril plug 16 into the first nostril. The operator may then adjust the air pressure delivered to the first nostril by adjusting power variation means 22. The operator then swallows, opening the Eustachian tube to allow equalization of middle ear pressure with the ambient pressure.

Figure 5:
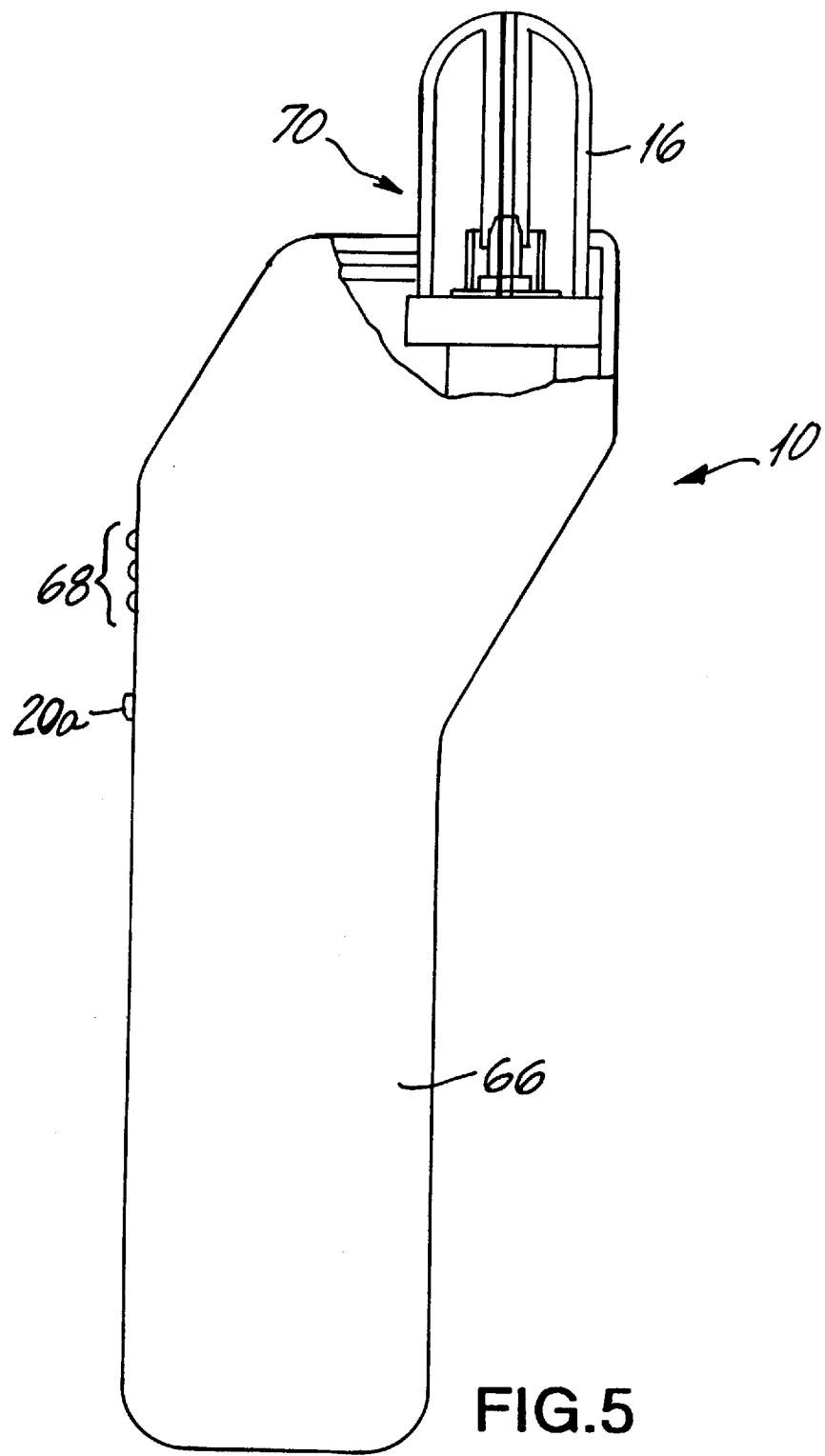
Figure 6:
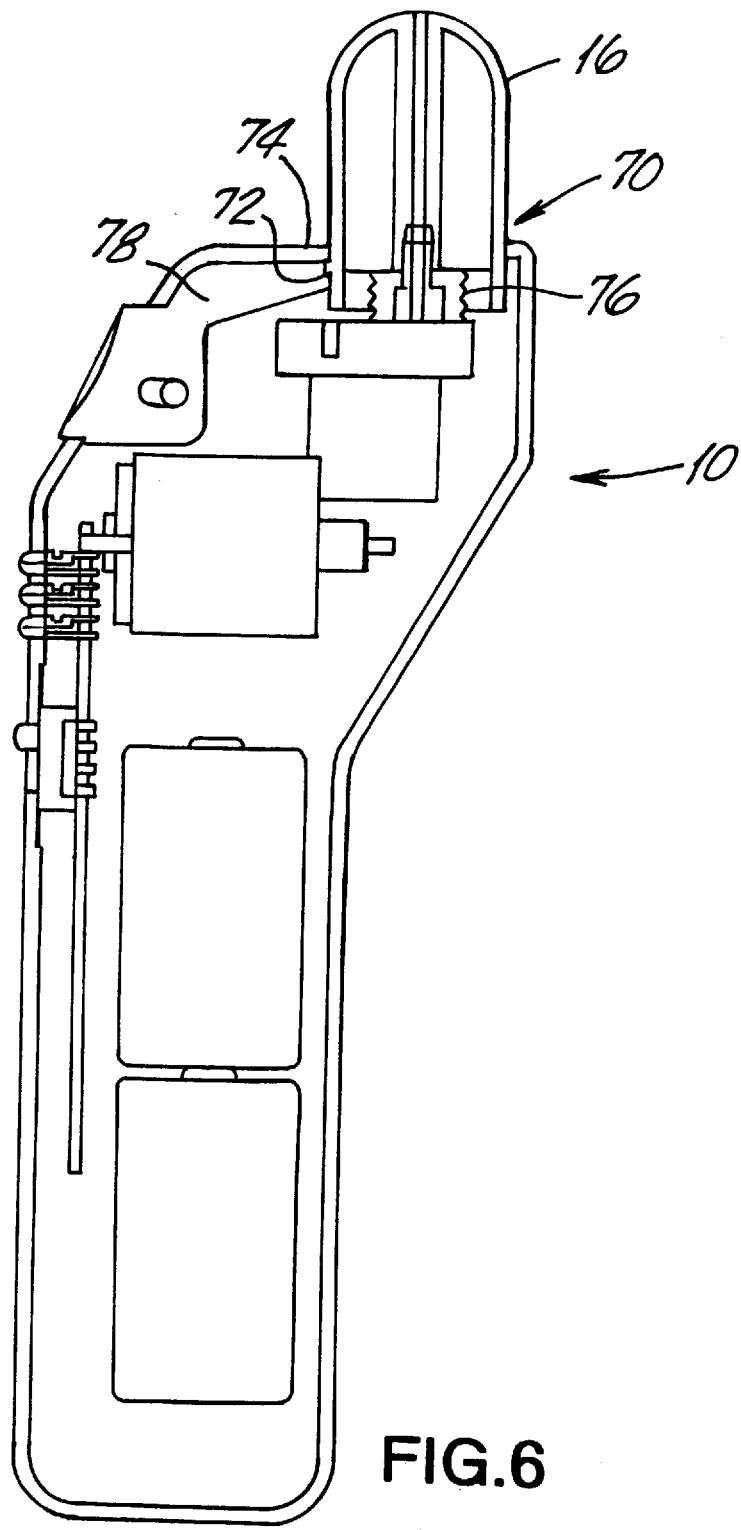
FIG. 6 is a side cross-sectional view of an alternate embodiment of the present invention which illustrates a cross-sectional view of a nostril plug.

Nostril plug 16 has an outer shape to accommodate various nostril sizes. Nostril plug 16 may be conically tapered, having an angle of inclination, θ, of approximately 70°, a base diameter of approximately of 1.0 inch tapering to a tip diameter of approximately 0.375 inches. The diameter of channel 44 is preferably approximately 0.0938 inches. Referring to FIGS. 5 and 6, nostril plug 16 may be cylindrically shaped having a spherically shaped top accommodate various nostril sizes.

The compressor 14 must generate sufficient air pressure at the exit of channel of 42 to operate effectively. The preferred minimum air pressure which the device must be able to create is approximately 0.5 pounds/inch$^2$ (p.s.i.). While the upper limit of pressure which the device can create may exceed the limit specified herein, it is believed, for the safety of the patient, that the pressure created by the device should not exceed approximately 3.5 p.s.i. Preferably, the maximum air pressure is approximately 2.0 p.s.i. The peak flow rate of air should be within the range of 0.5 liter/minute to 4.0 liters/minute. Preferably, the peak flow rate should be between 1.5 liters/minute and 2.0 liters/minute.

Referring to FIG. 5, an alternate embodiment of pressure equalizing apparatus 10 includes nostril plug 16, handle 66, multi-position switch 20a and operating display 68. Multi-position switch 20a replaces switch 20 and power variation device 22 previously discussed. Multi-position switch 20a is positioned relative to handle 66 to allow manipulation using a thumb which is associated with the hand which is used to hold apparatus 10. As a result, the user may support and control apparatus 10 using one hand.

Figure 7:
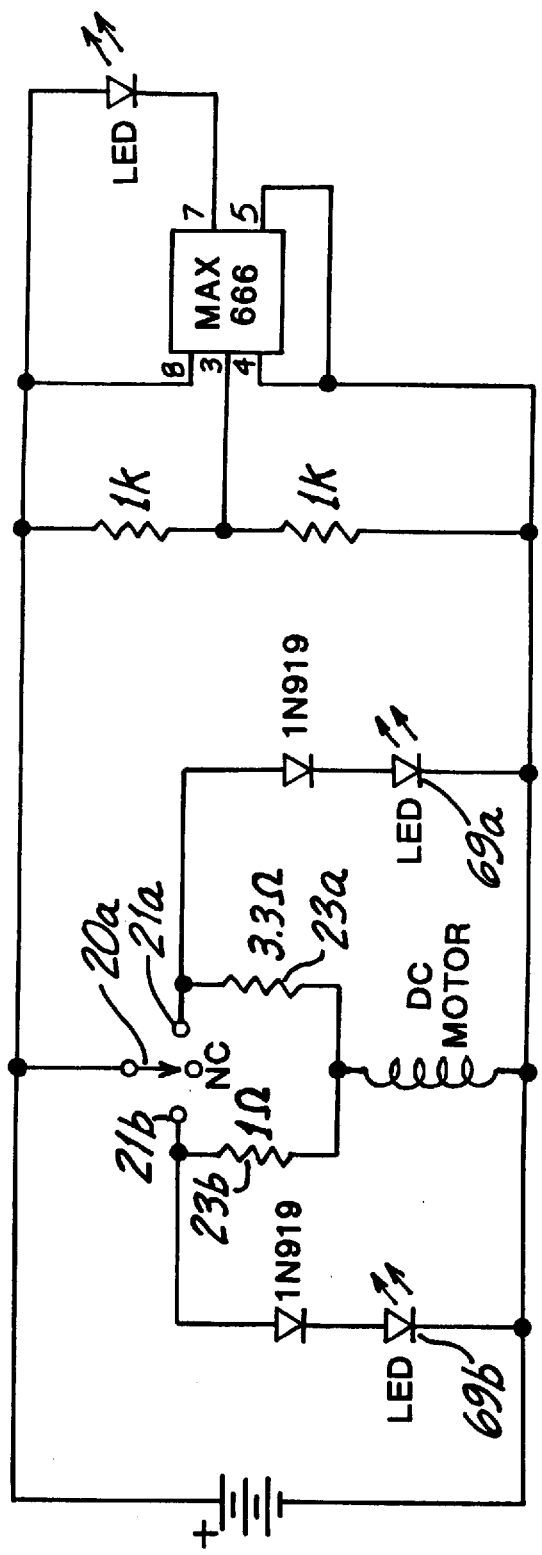
FIG. 7 is a schematic illustrating the electrical connections of one embodiment of the present invention.

Referring to FIG. 7, multi-position switch 20a may occupy one of three positions. In the first position, switch 20a contacts first element 21a to occupy a first operating state. The value of resistor 23a is selected to achieve the characteristics associated with the first operating state of the air flow source. In one embodiment, resistor 23a is a 3.3 ohm resistor intended to achieve an air flow rate of 1.0 liter/min. and maximum air delivery pressure of 1.5 p.s.i.

In the second position, switch 20a contacts second element 21b to occupy a second operating state. The value of resistor 23b is selected to achieve the characteristics associated with the second operating state. In one embodiment, resistor 23b is a 1.0 ohm resistor selected to achieve an air flow rate of 2.0 liters/min. and a maximum air delivery pressure of 3.0 p.s.i. Preferably, the first and second operating states are selected to achieve incremental operating states, i.e., the first operating state has an operating characteristic which is lower than that of the second operating state.

Operating display 68 may include any number of indicators which inform the operator of the status of the apparatus 10. For example, operating display 68 may provide an indicator which indicates that the switch 20 occupies the on position. In an embodiment having a multi-position switch 20a, any number of indicators may be provided to indicate which position is being occupied by switch 20a. For example, referring to FIG. 7, first and second positions of switch 20a cause LEDS 69a and 69b, respectively, to emit light.

In addition to multi-position switch 20a and associated indicators 69a, 69b, the circuitry provides for a battery low indicator. A commercially available chip, MAX666, two 1 kohm resistors and an LED are connected as illustrated in FIG. 7 to achieve the desired configuration of one embodiment.

Referring to FIG. 5, nostril plug 16 is removable from apparatus 10. Nostril plug 16 is fictionally fit into opening 70 of apparatus 10. Alternatively, plug 16 is in threaded engagement with mating threads on apparatus 10.

Referring to FIG. 6, nostril plug 16 includes shoulder 72 which, when inserted into opening 70, engages rim 74 of opening 70. A spring 76 is biased between nostril plug 16 and apparatus 10. Nostril plug removal element 78 is provided to disengage shoulder 72 and rim 74. As a result, spring 76 expels plug 16 from opening 70 once shoulder 72 disengages rim 74.

Preferably, nostril plug 16 is constructed from material making disposal and replacement thereof inexpensive.

In an alternate embodiment, an inhalable gas, stored in a container under pressure may be used in conjunction with a valve to provide a relatively constant flow of gas to a nostril plug.

In a further embodiment, a motorized fan may be used to replace the compressor to generate the necessary pressure or air flow.

While preferred embodiments of the present invention have been shown and described, it will be understood by those skilled in the art that various changes and modifications, could be made without varying from the scope of the present invention, including the incorporation of features discussed with respect to one embodiment into a device according to a different embodiment.

What is claimed is:

1. Apparatus for equalizing pressure in a middle ear comprising:

a hand held device having an exit port, an electric powered air source for providing a predetermined continuous flow of air at said exit port, said flow of air being at a substantially constant flow rate when unobstructed, said air source delivering said air at a pressure range having a predetermined upper limit, a removable sealing nostril plug adapted to be inserted into a nostril, said nostril plug having a channel therethrough, said nostril plug adapted to be mounted at said exit port to place said channel of said nostril plug in communication with said exit port, user actuated switch control coupled to said air source to turn said air source on and off to provide a user determined duration for said air flow.

2. The apparatus of claim 1 wherein said predetermined upper limit for the pressure of said air is 3.5 pounds per square inch.

3. The apparatus of claim 1 wherein said pressure range is between 1.0 and 3.0 pounds per square inch.

4. The apparatus of claim 1 further comprising:

operator actuated power level control coupled to said air source to adjust said unobstructed flow of air to a flow rate in the range of 1.0 liter per minute to 4.0 liters per minute.

5. The apparatus of claim 4 wherein said predetermined upper limit for the pressure of said air is 3.5 pounds per square inch.

6. The apparatus of claim 1 wherein said air source is battery powered.

7. The apparatus of claim 1 wherein said casing has a handle and said operator actuated switch control and power level control are on said handle to provide one-handed support and operation of said apparatus.

* * * * *